US006925389B2

(12) United States Patent
Hitt et al.

(10) Patent No.: US 6,925,389 B2
(45) Date of Patent: Aug. 2, 2005

(54) PROCESS FOR DISCRIMINATING BETWEEN BIOLOGICAL STATES BASED ON HIDDEN PATTERNS FROM BIOLOGICAL DATA

(75) Inventors: Ben A. Hitt, Severn, MD (US); Emanuel F. Petricoin, III, Dunkirk, MD (US); Peter J. Levine, Potomac, MD (US); Lance A. Liotta, Bethesda, MD (US)

(73) Assignees: Correlogic Systems, Inc.,, Bethesda, MD (US); The United States of America as Represented by the Department of Health and Human Services, Washington, DC (US)

( * ) Notice: Subject to any disclaimer, the term of this patent is extended or adjusted under 35 U.S.C. 154(b) by 299 days.

(21) Appl. No.: 09/906,661

(22) Filed: Jul. 18, 2001

(65) Prior Publication Data

US 2003/0004402 A1 Jan. 2, 2003
US 2005/0043593 A9 Jan. 2, 2003

Related U.S. Application Data

(60) Provisional application No. 60/289,362, filed on May 8, 2001, provisional application No. 60/278,550, filed on Mar. 23, 2001, provisional application No. 60/232,299, filed on Sep. 12, 2000, and provisional application No. 60/219,067, filed on Jul. 18, 2000.

(51) Int. Cl.[7] ..................... G01N 33/48; G01N 33/50; G06F 7/00; G06G 7/48
(52) U.S. Cl. ..................... 702/19; 702/20; 702/22; 702/27; 702/30; 702/32; 707/3; 707/102; 435/6; 435/7.1
(58) Field of Search ............. 702/19–32; 703/11; 707/3, 102; 435/6, 7.1

(56) References Cited

U.S. PATENT DOCUMENTS

| 4,122,343 | A | 10/1978 | Risby et al. |
| 4,697,242 | A | 9/1987 | Holland et al. |
| 4,881,178 | A | 11/1989 | Holland et al. |
| 5,136,686 | A | 8/1992 | Koza |
| 5,352,613 | A | 10/1994 | Tafas et al. |
| 5,649,030 | A | 7/1997 | Normile et al. |
| 5,687,716 | A | 11/1997 | Kaufmann et al. |
| 5,697,369 | A | 12/1997 | Long, Jr. et al. |
| 5,716,825 | A | 2/1998 | Hancock et al. |
| 5,790,761 | A | 8/1998 | Heseltine et al. |
| 5,839,438 | A | 11/1998 | Graettinger et al. |
| 5,905,258 | A | 5/1999 | Clemmer et al. |
| 5,946,640 | A | 8/1999 | Goodacre et al. |
| 5,974,412 | A | 10/1999 | Hazlehurst et al. |
| 6,025,128 | A | 2/2000 | Veltri et al. |
| 6,081,797 | A | 6/2000 | Hitt |
| 6,128,608 | A | 10/2000 | Barnhill |
| 6,157,921 | A | 12/2000 | Barnhill |
| 6,295,514 | B1 | 9/2001 | Agrafiotis et al. |
| 6,329,652 | B1 | 12/2001 | Windig et al. |
| 6,427,141 | B1 | 7/2002 | Barnhill |
| 6,558,902 | B1 | 5/2003 | Hillenkamp |
| 6,571,227 | B1 | 5/2003 | Agrafiotis et al. |
| 6,615,199 | B1 | 9/2003 | Bowman-Amuah |
| 6,675,104 | B2 | 1/2004 | Paulse et al. |
| 2002/0046198 | A1 * | 4/2002 | Hitt .............................. 706/20 |
| 2002/0138208 | A1 | 9/2002 | Paulse et al. |
| 2002/0193950 | A1 | 12/2002 | Gavin et al. |
| 2003/0054367 | A1 | 3/2003 | Rich et al. |
| 2003/0077616 | A1 | 4/2003 | Lomas |
| 2003/0134304 | A1 | 7/2003 | van der Greef et al. |

FOREIGN PATENT DOCUMENTS

| WO | WO 93/05478 A1 | 3/1993 |
| WO | WO 99/41612 | 8/1999 |
| WO | WO 99/47925 A2 | 9/1999 |
| WO | WO 99/58972 A1 | 11/1999 |
| WO | WO 00/49410 A3 | 8/2000 |
| WO | WO 00/55628 A1 | 9/2000 |
| WO | WO 01/20043 A1 | 3/2001 |
| WO | WO 01/31579 A2 | 5/2001 |
| WO | WO 01/31580 A2 | 5/2001 |
| WO | WO 01/84140 A2 | 11/2001 |
| WO | WO 02/059822 A2 | 8/2002 |
| WO | WO 02/088744 A2 | 11/2002 |
| WO | WO 03/031031 A1 | 4/2003 |

OTHER PUBLICATIONS

Lockhart, D.J. et al. Nature Jun. 15, 2000, vol. 405 pp. 827–836.*
Roses, A.D. Nature Jun. 15, 2000 pp. 857–865.*
Moler, E.J. et al. Physiol. Genomics Dec., 2000, vol. 4 pp. 109–126.*
Liotta et al. Genetics, Oct. 1, 2000, vol. 1 pp. 48–56.*
Jun Zhang, *Dynamics and Formation of Self–Organizing Maps*, in "Self–Organizing Map Formation: Foundations of Neural Computation," Oct. 2001, pp. 55–67 (Klaus Obermayer & Terrence J. Sejnowski eds.).
Ricketts et al., "*Towards the Automated Prescreening of Cervical Smears,*" Mar. 11, 1992, 4 pages, Applications of Image Processing in Mass Health Screening, IEE Colloquium.

(Continued)

Primary Examiner—Mary K. Zeman

(57) ABSTRACT

The invention describes a process for determining a biological state through the discovery and analysis of hidden or non-obvious, discriminatory biological data patterns. The biological data can be from health data, clinical data, or from a biological sample, (e.g., a biological sample from a human, e.g., serum, blood, saliva, plasma, nipple aspirants, synovial fluids, cerebrospinal fluids, sweat, urine, fecal matter, tears, bronchial lavage, swabbings, needle aspirantas, semen, vaginal fluids, pre-ejaculate.), etc. which is analyzed to determine the biological state of the donor. The biological state can be a pathologic diagnosis, toxicity state, efficacy of a drug, prognosis of a disease, etc. Specifically, the invention concerns processes that discover hidden discriminatory biological data patterns (e.g., patterns of protein expression in a serum sample that classify the biological state of an organ) that describe biological states.

48 Claims, No Drawings

OTHER PUBLICATIONS

Cairns et al., "Towards the Automated Prescreening of Breast X–Rays," Mar. 11, 1992, 5 pages, Applications of Image Processing in Mass Health Screening, IEE Colloquium.

Belic, "Neural Networks Methodologies for Mass Spectra Recognition," pp. 374–380.

Zhang, "Combining Multiple Biomarkers in Clinical Diagnostics—A Review of Methods and Issues," Tumor Markers: Physiology, Pathobiology, Technology, and Clinical Applicatin, 2002, 14 pages.

Jain et al., "Statistical Pattern Recognition: A Review," IEEE Transactions On Pattern Analysis and Machine Intelligence, vol. 22, No. 1, Jan. 2000, pp. 4–37.

Hackett et al., "Rapid SELDI Biomarker Protein Profiling of Serum from Normal and Prostate Cancer Patients," American Association for Cancer Research, vol. 41, Mar. 2000 (Abstract only), pp. 563–564.

Microsoft Press, Computer Dictionary: The Comprehensive Standard for Business, School, Library, and Home, Microsoft Press, 408.

Dhar et al., Seven Methods for Transforming Corporate Data Into Business Intelligence, Prentice Hall, pp. 52–76.

Reed, "Trends in Commercial Bioinformatics," Oscar Gruss Biotechnology Review, Mar. 2000, 20 pages.

Gaskell, "Electrospray: Principles and Practice," Journal of Mass Spectrometry, vol. 32, pp. 677–688 (1997), John Wiley & Sons, Ltd.

Lewis, "An Introduction to Classification and Regression Tree (CART) Analysis," presented at 2000 Annual Meeting of the Society for Academic Emergency Medicine in San Francisco, California, pp. 1–14, 2000.

Hess et al., "Classification and Regression Tree Analysis of 1000 Consecutive Patients with Unknown Primary Carcinoma," Clinical Cancer Research, vol. 5, pp. 3403–3410, Nov. 1999.

Schroll et al., "Applications of Artificial Intelligence for Chemical Inference, III. Aliphatic Ethers Diagnosed by Their Low–Resolution Mass Spectra and Nuclear Magnetic Resonance Data," Journal of the American Chemical Society, Dec. 17, 1969, pp. 7440–7445.

Crawford et al., "Computer Methods in Analytical Mass Spectrometry; Empirical Identification of Molecular Class," 6 pages, 1968.

Jurs et al., "Computerized Learning Machines Applied to Chemical Problems; Molecular Formula Determination from Low Resolution Mass Spectrometry," Analytical Chemistry, vol. 41, No. 1, Jan. 1969, pp. 21–27.

Meuzelaar et al., "A Technique for Fast and Reproducible Fingerprinting of Bacteria by Pyrolysis Mass Spectrometry," Analytical Chemistry, vol. 45, No. 3, Mar. 1973, pp. 587–590.

"Constraints on "Learning Machine" Classification Methods," Analytical Chemistry, vol. 48, No. 14, Dec. 1976, pp. 2265–2268, Gray, N.A.B.

Lowry et al., "Comparison of Various K–Nearest Neighbor Voting Schemes with the Self–Training Interpretive and Retrieval System for Identifying Molecular Substructures from Mass Spectral Data," Analytical Chemistry, vol. 49, No. 12, Oct. 1977, pp. 1720–1722.

Macfie et al., "Use of Canonical Variates Analysis in Differentiation of Bacteria by Pyrolysis Gas–Liquid Chromatography," Journal of General Microbiology (1978), 104, pp. 67–74, Great Britain.

Atkinson et al., "Statistical Techniques for Diagnosing CIN Using Fluorescence Spectroscopy: SVD and CART," Journal of Cellular Biochemistry, Supplement 23, pp. 125–130 (1995).

Dzeroski et al., "Diterpene Structure Elucidation from $^{13}C$ NMR–Spectra with Machine Learning," Intelligent Data Analysis in Medicine and Pharmacology,pp. 207–225, Kluwer Academic Publishers, 1997.

Voorhees et al., "Approaches to Pyrolysis/Mass Spectrometry Data Analysis of Biological Materials," Computer–Enhanced Analytical Spectroscopy,vol. 2, pp. 259–275, Plenum Press, New York, 1990.

Reibnegger et al., "Neural networks as a tool for utilizing laboratory information: Comparison with linear discrminant analysis and with classification and regression trees," Proc. Natl. Acad. Sci. USA, vol. 88, pp. 11426–11430, Dec. 1991.

Jellum et al., "Mass Spectrometry in Diagnosis of Metabolic Disorders," Biomedical and Environmental Mass Spectrometry, vol. 16, pp. 57–62 (1988).

Wythoff et al., "Spectral Peak Verification and Recognition Using a Multilayered Neural Network," Analytic Chemistry, vol. 62, No. 24, pp. 2702–2709, Dec. 15, 1990.

Meyer et al., "Identification of the $^1H$–NMR Spectra of Complex Oligosaccharides with Artificial Neural Networks, "Science, vol. 251, pp. 542–544, Feb. 1991.

Furlong et al., "Neural Network Analysis of Serial Cardiac Enzyme Data: A Clinical Application of Artificial Machine Intelligence," A.J.C.P., vol. 96, No. 1, pp. 134–141, Jul., 1991.

Cicchetti, "Neural Networks and Diagnosis in the Clinical Laboratory: State of the Art," Clinical Chemistry, vol. 38, No. 1, pp. 9–10 (1992).

Ashfaq et al., "Evaluation of PAPNET™ System for Rescreening of Negative Cervical Smears," Diagnostic Cytopathology, vol. 13, No. 1, pp. 31–36, 1995.

Malins et al., "Models of DNA structure achieve almost perfect discrimination between normal prostrate, benign prostatic hyperplasia (BPH), and adenocarcinoma and have a high potential for predicting BPH and prostate cancer," Proc. Natl. Acad. Sci. USA, vol. 94, pp. 259–264, Jan. 1997.

Kohno et al., "Quantitative Analysis of Scintiscan Matrices by Computer," Japanese Journal of Medical Electronics and Biological Engineering, pp. 22–29, Aug. 1974, English Abstract.

Salford Systems, "Salford Systems White Paper Series," 17 pages, 2000.

Berikov et al., "Regression trees for analysis of mutational spectra in nucleotide sequences," Bioinformatics, vol. 15, Nos. 7/8, 1999, pp. 553–562.

Breiman et al., Classification and Regression Trees, pp. 174–265, Chapman & Hall/CRC, 1998.

Halket et al., "Deconvolution Gas Chromatography/Mass Spectrometry of Urinary Organic Acids—Potential for Pattern Recognition and Automated Identification of Metabolic Disorders," Rapid Communications in Mass Spectrometry, vol. 13, pp. 279–284 (1999).

Eghbaldar et al., "Identification of Structural Features from Mass Spectrometry Using a Neural Network Approach: Application to Trimethylsilyl Derivatives Used for Medical Diagnosis," J. Chem. Inf. Comput. Sci., vol. 36, No. 4, 1996, pp. 637–643.

Babaian, et al., "Performance of a Neural Network in Detecting Prostate Cancer in the Prostate–Specific Antigen Reflex Range of 2.5 to 4.0 ng/ml," *Urology*, vol. 56(6), 2000, pp. 1000–1006.

Tong et al., "Mass Spectral Search method using the Neural Network approach," *International Joint Conference on Neural Networks*, Washington, DC Jul. 10–16, 1999, Proceedings, vol. 6 of 6, pp. 3962–3967.

Tong et al., "Mass spectral search method using the neural network approach," *Chemometrics and Intelligent Laboratory Systems*, vol. 49 (1999), pp. 135–150.

Hashemi et al., "Identifying and Testing of Signatures for Non–Volatile Biomolecules Using Tandem Mass Spectra," *SIGBIO Newsletter*, vol. 15, No. 3, pp. 11–19, Dec. 1995.

Belic et al., "Neural network methodologies for mass spectra recognition," *Vacuum*, vol. 48, No. 7–9, pp. 633–637, 1997.

Werther et al., "Classification of mass spectra; a comparison of yes/no classification methods for the recognition of simple structural properties," *Chemometrics and Intelligent Laboratory Systems*, vol. 22 (1994), pp. 63–76.

Astion et al., "The Application of Backpropagation Neural Networks to Problems in Pathology and Laboratory Medicine," *Arch Pathol Lab Med*, vol. 116, Oct. 1992, pp. 995–1001.

Taylor et. al., "The deconvolution of pyrolysis mass spectra using genetic programming: application to the identification of some *Eubacterium* species," *FEMS Microbiology Letters* 160 (1998) pp. 237–246.

Goodacre et al., "Discrimination between methicillin–resistant and methicillin–susceptible *Staphylococcus aureus* using pyrolysis mass spectrometry and artificial neural networks," *Journal of Antimicrobial Chemotherapy*, vol. 41, pp. 27–34 (1998).

Chun et al., "Long–term Identification of Streptomycetes Using Pyrolysis Mass Spectrometry and Artificial Neural Networks," *Zbl. Bakt.* 185, pp. 258–266 (1997).

Kenyon et al., "Application of Neural Networks to the Analysis of Pyrolysis Mass Spectra," *Zbl. Bakt.* 285, pp. 267–277 (1997).

Nilsson et al., "Classification of Species in the Genus *Penicillium* by Curie Point Pyrolysis/Mass Spectrometry Followed by Multivariate Analysis and Artificial Neural Networks," *Journal of Mass Spectrometry*, vol. 31, pp. 1422–1428 (1996).

Goodacre et al., "Sub–species Discrimination, Using Pyrolysis Mass Spectrometry and Self–organising Neural Networks, of *Propionibacterium acnes* Isolated from Normal Human Skin," *Zbl. Bakt.* 284, pp. 501–515 (1996).

Goodacre et al., "Quantitative Analysis of Multivariate Data Using Artificial Neural Networks: A Tutorial Review and Applications to the Deconvolution of Pyrolysis Mass Spectra," *Zbl. Bakt.* 284 pp. 516–539 (1996).

Goodacre et al., "Identification and Discrimination of Oral Asaccharolytic *Eubacterium* spp. by Pyrolysis Mass Spectrometry and Artificial Neural Networks," *Current Microbiology*, vol. 32, pp. 77–84, (1996).

Goodacre et al., "Correction of Mass Spectral Drift Using Artificial Neural Networks," *Anal. Chem.*, 1996, vol. 68, pp. 271–280.

Freeman et al., "Resolution of batch variation in pyrolysis mass spectrometry of bacterial by the use of artificial neural network analysis," *Antonie van Leeuwenhoek* vol. 68, pp. 253–260, 1995, Kluwer Academic Publishers, The Netherlands.

Chace et al., "Laboratory integration and utilization of tandem mass spectrometry in neonatal screening: a model for clinical mass spectrometry in the next millennium," *Acta Paediatr. Suppl.* 432, pp. 45–47 (1999).

Curry et al., "MSnet: A Neural Network That Classifies Mass Spectra," 32 pages, 1990.

Shaw et al., "Infrared Spectroscopy of Exfoliated Cervical Cell Specimens," *Analytical and Quantitative Cytology and Histology*, vol. 21, No. 4, Aug. 1999, pp. 292–302.

Prior et al., "Potential of Urinary Neopterin Excretion in Differentiating Chronic Non–A, Non–B Hepatitis from Fatty Liver," *The Lancet*, Nov. 28, 1987, pp. 1235–1237.

Yates, III, "Mass Spectrometry and the Age of the Proteome," *Journal of Mass Spectrometry*, vol. 33, pp. 1–19 (1998).

Hausen et al., "Determination of Neopterine in Human Urine by Reversed–Phase High–Performance Liquid Chromatography," *Journal of Chromatography*, vol. 227, pp. 61–70 (1982).

Shevchenko et al., "MALDI Quadupole Time–of–Flight Mass Spectrometry: A Powerful Tool for Proteomic Research," *Anaytical Chemistry*, vol. 72, No. 9, pp. 2132–2141, May 1, 2000.

Dudoit et al., "Comparison of Discrimination Methods for the Classification of Tumors Using Gene Expression Data," 43 pages, Jun. 2000.

Dudoit et al., "Comparison of discrimination methods for the classification of tumors using gene expression data," UC Berkeley, Mar. 7, 2000, pp. 1–51.

Nikulin et al., "Near–optimal region selection for feature space reduction: novel preprocessing methods for classifying MR spectra," *NMR Biomedicine*, vol. 11, pp. 209–216 (1998).

Alaiya et al., "Classification of Human Ovarian Tumors Using Multivariate Data Analysis of Polypeptide Expression Patterns,"*Int. J. Cancer*, vol. 86, pp. 731–736 (2000).

Bailey–Kellogg et al., "Reducing Mass Degeneracy in SAR by MS by Stable Isotopic Labeling," *Journal of Computational Biology*, vol. 8, No. 1, pp. 19–36 (2001).

Caprioli et al., "Molecular Imaging of Biological Samples: Localization of Peptides and Proteins Using MALDI–TOF MS," *Analytical Chemistry*, vol. 69, No. 23, pp. 4751–4760, Dec. 1, 1997.

George, "A Visualization and Design Tool (AVID) for Data Mining with the Self–Organizing Feature Map," *International Journal on Artificial Intelligence Tools*, vol. 9, No. 3, pp. 369–375, (2000).

Kohavi, et al., "Wrappers for feature subset selection," *Artificial Intelligence*, vol. 97, pp. 273–324, (1997).

Marvin et al., "Characterization of a novel *Sepia officinalis* neuropeptide using MALDI–TOL MS and post–source decay analysis," *Peptides*, vol. 22, pp. 1391–1396, (2001).

Oh et al., "A database of protein expression in lung cancer," *Proteomics*, vol. 1, pp. 1303–1319, (2001).

Strouthopoulos et al., "PLA using RLSA and a neural network," *Engineering Applications of Artificial Intelligence*, vol. 12, pp. 119–138, (1999).

Taylor et al., "The deconvolution of pyrolysis mass spectra using genetic programming: application to the identification of some *Eubacterium* species," *FEMS Microbiology Letters*, vol. 160, pp. 237–246, (1998).

Claydon, MA "The rapid identification of intact microorganisms using mass spectrometry," 1 page (Abstract) from Nat. Biotechnol. 14(11):1584–86 (Nov. 1996).

Yao et al. "Evolving Artificial Neural Networks for Medical Applications," Proceedings of the First Korea–Australia Joint Workshop on Evolutionary Computation, pp. 1–16, (Sep. 1995).

Pei et al. "Feature Extraction Using Genetic Algorithms," Proceedings of the $1^{st}$ International Symposium on Intelligent Data Engineering and Learning, IDEAL '98, Springer, Hong Kong, Oct. 1998 pp. 371–384.

Goodacre et al. "Rapid Identification of urinary tract infection bacteria using hyperspectral whole–organism fingerprinting and artificial neural networks.," Microbiology 144: 1157–70 (1998).

Loging, TW et al., "Identifying Potential Tumor Markers and Antigens by Database Mining and Rapid Expression Screening," Genome Research, 10(9):1393–1402 (Sep. 2000).

Krishnamurthy, T. et al. "Detection of Pathogenic and Non-Pathogenic Bacteria by Matrix–assisted Laser Desorption-.Ionization Time–of–flight Mass Spectrometry," Rapid Comms. in Mass Spectrometry, vol. 10, 883–888 (1996).

Adam, B–L et al., "Serum Protein Fingerprinting Coupled with a Pattern–matching Algorithm Distinguishes Prostate Cancer from Benign Prostate Hyperplasin and Healthy Men," Cancer Research 62, 3609–3614 (Jul. 1, 2002).

Li, J. et al. "Proteomics and Bioinformatics Approaches for Identification of Serum Biomarkers to Detect Breast Cancer," Clinical Chemistry 48:8, 1296–1304 (2002).

Petricion III, E.F. et al., "Use of proteomic patterns in serum to identify ovarian cancer," The Lancet, vol. 359, 572–577 (Feb. 16, 2002).

Brown, M.P.S. et al. "Knowledge–based analysis of microarray gene expression data by using support vector machines," PNAS vol. 97, No. 1, pp. 262–267 (Jan. 4, 2000).

Kiem, H. & Phuc, D, "Using Rough Genetic and Kohonen's Neural Network for Conceptual Cluster Discovery in Data Mining," New Directions in Rough Sets, Data Mining and Granular–Soft Computing. International Workshop, RSFDGRC Proceedings, pp. 448–452 (Nov. 9, 1999).

Chang, E.I et al., "Using Genetic Algorithms to Select and Create Features for Pattern Classification," UCNN International Joint Conf. on Neural Networks, pp. III–747 to III–752 (Jan. 8, 1991).

Rosty C. et al., "Identification of Hepatocarcinoma–Intestine–Pancreas/Pancreatis–associated Protein I as a Biomarker for Pancreatic Ductal Adenocarcinoma by Protein Biochip Technology," Cancer Research 62:1868–75 (Mar. 15, 2002).

Claydon, M.A., "The rapid identification of intact microorganisms using mass spectrometry," Nature Biotech. 14:1584–1586 (Nov. 1996).

Bittl, J.A., "From Confusion to Clarity: Direct Thrombin Inhibitors for Patients with Heparin–Induced Thrombocytopenia," Cath. and Cardio. Interventions 52:473–475 (2001).

Paweletz, C.P., "Rapid Protein Display Profiling of Cancer Progression Directly from Human Tissue Using a Protein Biochip," Drug Development Research 49:34–42 (2000).

Ciphergen European Update, 1:1–4 (2001).

Kohonen, T. Self Organizing Maps (Springer 2001), pp. 1–70.

Kohonen, T. "Self–Organization and Associative Memory" (Springer 1988), pp. 30–67.

Holland, J.H., "Adaption in Natural and Artificial Systems: An Introductory Analysis with Applications to Biology, Control, and Artificial Intelligence" (MIT Press 2001), pp. 1–31; 89–120.

* cited by examiner

PROCESS FOR DISCRIMINATING BETWEEN BIOLOGICAL STATES BASED ON HIDDEN PATTERNS FROM BIOLOGICAL DATA

This application claims benefit under 35 U.S.C. sec. 119(e)(1) to U.S. Provisional Patent Application Ser. No. 60/232,299, filed Sep. 12, 2000, U.S. Provisional Patent Application Ser. No. 60/278,550, filed Mar. 23, 2001, which is hereby incorporated by reference in its entirety, U.S. Provisional Patent Application Ser. No. 60/219,067, filed Jul. 18, 2000, which is hereby incorporated by reference in its entirety, and U.S. Provisional Patent Application Ser. No. 60/289,362, filed May 8, 2001, which is hereby incorporated by reference in its entirety.

STATEMENT OF FEDERALLY SPONSORED RESEARCH OR DEVELOPMENT

The research work described here was supported under a Cooperative Research and Development Agreement (CRADA) between the US Government and Correlogic Systems, Inc.

I. FIELD OF THE INVENTION

The field of the invention concerns a process for determining a biological state through the discovery and analysis of hidden or non-obvious, discriminatory biological data patterns. The biological data can be from health data, clinical data, or from a biological sample, (e.g., a biological sample from a human, e.g., serum, blood, saliva, plasma, nipple aspirants, synovial fluids, cerebrospinal fluids, sweat, urine, fecal matter, tears, bronchial lavage, swabbings, needle aspirantas, semen, vaginal fluids, pre-ejaculate, etc.), etc. which is analyzed to determine the biological state of the donor. The biological state can be a pathologic diagnosis, toxicity state, efficacy of a drug, prognosis of a disease, etc.

Specifically, the invention concerns analytical methods that a) discover hidden discriminatory biological data patterns (e.g., patterns of protein expression in a serum sample that classify the biological state of an organ) that are subsets of the larger data stream, said discrimination implying the ability to distinguish between two or more biological states in a learning set of data and b) the application of the aforementioned patterns to classify unknown or test samples. More specifically, the invention concerns a method for analysis of a data stream, which is derived from a physical or chemical analysis of molecules (e.g., proteins, peptides, DNA, RNA, etc.) in the biological sample (e.g., a mass spectrum analysis of the sample).

These patterns are defined as "hidden" because they are often buried within a larger highly complex data set and are not obvious or apparent to the eye or other current classification systems. The pattern itself can be defined as the combination of three or more values such that the position of the vectors in an n-dimensional space is discriminatory between biological states even when individual values may not be discriminatory. The discriminatory patterns of the invention are novel because they can be defined without any knowledge of the identity or relationship between the individual data points in the biological data or any knowledge of the identity or relationship between the molecules in the biological samples.

One analytical method to discover such biological states comprises the application of two related heuristic algorithms, a learning algorithm and a diagnostic algorithm, wherein the parameters of the diagnostic algorithm are set by the application of the learning algorithm to a learning set of data such that two or more biological states may be distinguished. Such biological states may be the presence or absence of a disease, efficacy or non-efficacy of a drug, toxicity or non-toxicity of a drug, etc. Although the invention is generic, specific implementations for diagnosis of various cancers (including, but not limited to carcinomas, melanomas, lymphomas, sarcomas, blastomas, leukemias, myelomas, neural tumors, etc., and cancers of organs like the ovary, prostate, and breast.), presence of a pathogen, and toxicity are disclosed. The preferred embodiment of the invention is the discovery and use of molecular patterns that reflect the current or future biological state of an organ or tissue. Another embodiment of the invention is the combination of data describing the molecular patterns of a biological state with other non-biological or clinical data (e.g., psychiatric questioning) to yield a classification describing the health of a patient.

II. BACKGROUND OF THE INVENTION

The detection of changes in biological states, particularly the early detection of diseases has been a central focus of the medical research and clinical community. The prior art includes examples of efforts to extract diagnostic information from the data streams formed by physical or chemical analysis of tissue samples. These techniques are generically termed "data-mining." The data streams that have been mined are typically of two forms: analysis of the levels of mRNA expression by hybridization to DNA oligonucleotide arrays ("DNA microarrays") and analysis of the levels of proteins present in a cell or in a serum sample, wherein the proteins are characterized either by molecular weight using mass spectroscopy or by a combination of molecular weight and charge using a 2-D gel technique.

Rajesh Parekh and colleagues have described protein based data-mining diagnosis of hepatocellular cancer using serum or plasma samples (WO 99/41612), breast cancer using tissue samples (WO 00/55628) and rheumatoid arthritis using serum or plasma samples (WO 99/47925). In each publication, a two dimensional gel analysis is performed. The analysis consists of measuring the levels of individual proteins as determined by the 2-D gels and identifying those proteins that are elevated or depressed in the malignant as compared to the normal tissue.

Liotta and Petricoin (WO 00/49410) provide additional examples of protein based diagnostic methods using both 2-D gels and mass spectroscopy. However, the analysis of Liotta and Petricoin is similar to Parekh in that it consists of a search for specific tumor markers. Efforts to identify tumor markers have also been performed using DNA microarrays. Loging, W. T., 2000, Genome Res. 10, 1393–02, describes efforts to identify tumor markers by DNA microarrays in glioblastoma multiforme. Heldenfalk, I., et al., 2001, New England J. Med. 344, 539, report efforts to identify tumor markers that distinguish the hereditary forms of breast cancer resulting from BRCA1 and BRCA2 mutations from each other and from common idiopathic breast cancer by data-mining of DNA microarray data.

Alon et al., 1999, PNAS 96, 6745–50, describe the use of DNA microarray techniques to identify clusters of genes that have coordinated levels of expression in comparisons of colonic tumor samples and normal colonic tissue. These studies did, in fact, identify genes that were relatively over or under expressed in the tumor compared to normal tissue. However, the clustering algorithm was not designed to be able to identify diagnostic patterns of gene expression other than a tumor marker type pattern.

Data-mining efforts directed towards indicators other than tumor markers have been used for diagnosis. These efforts routinely employ pattern recognition methods to identify individual diagnostic markers or classify relationships between data sets. The use of pattern recognition methods to classify genes into categories based on correlated expression under a variety of different conditions was pioneered by Eisen, M., et al., 1998, PNAS 95, 14863–68; Brown, MPS, et al., 2000, PNAS 97, 262–67 and Alter, O., et al., 2000, PNAS 97, 10101–06. In general, these techniques use a vector space in which each vector corresponds to a gene or location on the DNA micro array. Each vector is composed of scalars that individually correspond to the relative levels of expression of the gene under a variety of different conditions. Thus, for example, Brown et al. analyzes vectors in a 79 dimension vector space where each dimension corresponds to a time point in a stage of the yeast life-cycle and each of 2,467 vectors correspond to a gene. The pattern recognition algorithms are used to identify clusters of genes whose expression is correlated with each other. Because the primary concern is the correlation of gene expression, the metric that is employed in the pattern recognition algorithms of Eisen et al. and related works is a Pearson coefficient or inner product type metric, not a Euclidean distance metric. Once clustering is established, the significance of each cluster is determined by noting any common, known properties of the genes of a cluster. The inference is made that the heretofore uncharacterized genes found in the same cluster may share one or more of these common properties.

The pattern recognition techniques of Eisen et al. were applied by Alizadeh and Staudt to the diagnosis of types of malignancy. Alizadeh and Staudt began by constructing vectors, each corresponding to a gene, having scalars that correspond to the relative level of expression of the gene under some differentiation condition, e.g., resting peripheral blood lymphocyte or mitogen stimulated T cells. The pattern recognition algorithm then clusters the genes according to the correlation of their expression and defines a pattern of expression characteristic of each differentiation state. Samples of diffuse large B-cell lymphomas (DLBCL) were then analyzed by hybridization of mRNA to the same DNA microarrays as used to determine the gene clusters. DLBCL were found to have at least two different gene expression patterns, each characteristic of a normal differentiation state. The prognosis of the DLBCL was found to correlate with the characteristic differentiation state. Thus, the diagnostic question posed and answered in Alizadeh and Staudt was not benign or malignant but rather of determining the type or subtype of malignancy by identifying the type of differentiated cell having a pattern of gene expression most similar to that of the malignancy. Alizadeh et al., 2000, Nature 403, 503–511. Similar techniques have been used to distinguish between acute myeloid leukemia and acute lymphocytic leukemia. Golub, T. R., et al., 1999, Science 286, 531–537.

Accordingly, it can be seen that data-mining methods based on the physical or chemical analyses having large numbers, i.e., greater than 1,000, of data points consist of two types: data-mining to identify individual markers such as genes or proteins having expression levels that are increased or suppressed in malignant cells of a defined type compared to normal cell; and data-mining wherein a pattern of known gene expression characteristic of a normal differentiated cell type is used to classify a known malignant cell according to the normal cell type it most closely resembles.

Thus, there is a need for methods that can determine biological states using biological data other than single markers (such as tumor markers), or gene expression clusters. Usually, the role that single markers play in the pathology of a disease must be known and established, quite often at great cost, prior to the analysis of a biological sample. Additionally, these markers are often localized in internal organs or tumors, and complex, invasive, localized biopsies must be performed to obtain biological samples containing such markers. Given the complexity of biological states such as a disease there is an exceptional need for the ability to diagnose biological states using complex data inherent to such biological states without prior extensive knowledge of the relationship of molecules present in such samples to each other.

Additionally, gene expression cluster analysis is limited in scope because such analysis incorporates an analysis of all expressed genes irrespective of whether the expression of such genes is causative or merely influenced by the causative action of those genes that are characteristic of the biological state. The clustering analysis does not incorporate solely those genes that are characteristic of the biological state of interest, but uses the entire range of data emanating from the assay, thus making it complex and cumbersome. Furthermore, gene expression analysis must involve nucleic acid extraction methods, making it complex, and time-consuming. Pattern recognition algorithms when applied are also rendered difficult because the correlation of gene expression that is employed is a complex Pearson coefficient or inner product type metric, and not a simple Euclidean distance metric.

In contrast to the prior art, the current invention discovers optimal hidden molecular patterns as subsets within a larger complex data field, whereby the pattern itself is discriminatory between biological states. Thus, the current invention avoids all the aforementioned problems associated with the analytical methods disclosed in the prior art, and has the ability to discover heretofore unknown diagnostic patterns. Such hidden molecular patterns are present in data streams derived from health data, clinical data, or biological data. Biological data may be derived from simple biological fluids, such as serum, blood, saliva, plasma, nipple aspirants, synovial fluids, cerebrospinal fluids, sweat, urine, fecal matter, tears, bronchial lavage, swabbings, needle aspirantas, semen, vaginal fluids, pre-ejaculate, etc., making routine sampling easy, although the expression of such molecular patterns are characteristic of disease states of remote organs. No prior knowledge of specific tumor markers or the relationship of molecules present in the biological sample to each other is required or even desired. The current invention also discloses methods of data generation and analysis. Such methods of data analysis incorporate optimization algorithms in which the molecular patterns are recognized, and subjected to a fitness test in which the fitness pattern that best discriminates between biological states is chosen for the analysis of the biological samples.

III. SUMMARY OF THE INVENTION

The invention comprises the use of pattern discovery methods and algorithms to detect subtle, if not totally hidden, patterns in the expression of certain molecules in biological samples that are potentially diagnostic in nature, or predictive of a biological state. In one embodiment of the invention such patterns of molecular expression are patterns of protein expression, particularly patterns of low molecular weight proteins (i.e. less than 20,000 Da). Such hidden patterns of protein expression may be obtained from only a sub-set of the total data-stream provided to the algorithm, several subsets, or may be obtained from an analysis of the total data stream. The pattern can be defined as a vector of three or more values such that the position of the vectors in an n-dimensional space is discriminatory between biological states even when individual values may not be discriminatory. The molecules of interest may be any relevant biological material such as proteins (full, cleaved, or partially expressed), peptides, phospholipids, DNA, RNA, etc.

The discriminatory patterns that discriminate between biological states are often small subsets of data hidden in the larger data stream derived from physical or chemical analysis of the biological sample. Thus, in order to find such discriminatory patterns that distinguish between biological states, a means for finding an optimal set of features that make up the discriminatory pattern is required. The invention incorporates the process for finding this optimal set of features. A number of feature selection methods for discriminatory patterns may be used to practice the invention with varying degrees of classification success. These include, but are not limited to, statistical methods, stepwise regression methods, linear optimization methods, etc. However, statistical methods have some limitations in that they are often linear, at least in their simple, well-known forms such as multivariate linear regressions. Furthermore, statistical models tend not to be robust with respect to non-linear data. The number of independent variables a statistical model can successfully employ is generally ten or less, with a practical preferred limit of five or six. The preferred embodiment uses a method that couples the genetic algorithm, an evolutionary computation method, directly to an adaptive pattern recognition algorithm to efficiently find the optimal feature set. See U.S. Patent Application titled "Heuristic Method of Classification," (filing date: Jun. 19, 2001, claiming priority of application Ser. No. 60/212,404, filed Jun. 19, 2000).

One method disclosed by this invention consists of two related heuristic algorithms, a diagnostic algorithm and a learning algorithm. The diagnostic algorithm is generated by the application of the learning algorithm to a learning (or training) data set. The learning data set is a data set formed from biological samples for which the biological state of interest is provided for the pattern discovery operation. For instance, the learning data set may comprise data taken from the sera of individuals with an established biopsy diagnosis, e.g., a benign tumor and a malignant tumor. This would enable the learning algorithm to find a signature pattern of proteins that could discriminate normal from cancerous sera samples.

In one embodiment, the method according to the invention begins by subjecting a biological sample to a high throughput physical or chemical analysis to obtain a data stream. Such data streams include, but are not limited to, mass spectral data of proteins found in the sample or in the intensity of mRNA hybridization to an array of different test polynucleotides. Generally, the data stream is characterized by a large number (10,000 or more) of intensities which are generated in a way that allow for the corresponding individual datum in data streams of different samples to be identified.

The first step of the diagnostic method is to calculate a vector, i.e., an ordered set of a small number (between 2 and 20100, more typically between 5 and 208) that is characteristic of the data stream. The transformation of the data steam into a vector is termed "abstraction." In the present embodiments, abstraction is performed by selection of a small number of specific intensities from the data stream.

The second step of the diagnostic method is to determine in which, if any, data cluster the vector rests. Data clusters are mathematical constructs that are the multidimensional equivalents of non-overlapping "spheres" of fixed size in the vector space. Such data clusters are known as hyperspheres. The location and associated diagnosis of each data cluster is determined by the learning algorithm from the training data set. If the vector of the biological sample lies within a known cluster, the sample is given the diagnosis associated with that cluster. If the sample vector rests outside of any known cluster a diagnosis can be made that the sample does not meet that classification criteria or that it is of an unspecified atypia, i.e., an "a typical sample, NOS." For example, if a biological sample taken from a patient does not meet the classification of a malignant state for a specified cancer, it will be classified as non-malignant non-normal or of an unspecified atypia, "a typical sample, NOS."

The learning algorithm utilizes a combination of known mathematical techniques and two pre-set parameters. The user pre-sets the number of dimensions of the vector space and the size of the data clusters. Typically, the vector space is a normalized vector space such that the variation of intensities in each dimension is constant. Thus, the size of the cluster can be expressed as a minimum percent similarity among the vectors resting within the cluster.

In one embodiment, the learning algorithm contains of two generic parts, which have been developed by others and are well known in the field—a genetic algorithm (J. H. Holland, Adaptation in Natural and Artificial Systems, MIT Press 1992) and a self-organizing adaptive pattern recognition system (T. Kohonen, Self Organizing and Associative Memory, 8 Series in Information Sciences, Springer Verlag, 1984; Kohonen, T, Self-organizing Maps, Springer Verlag, Heidelberg 1997). Genetic algorithms organize and analyze complex data sets as if they were information comprised of individual elements that can be manipulated through a computer driven natural selection process.

In the present invention, the search for hidden or subtle patterns of molecular expression that are, in and of themselves "diagnostic" is qualitatively different from those generated by prior art implementations of learning algorithms or data-mining techniques. Previous implementations of data-mining have identified specific molecular products that are indicative of a classification, e.g., proteins or transcripts that are elevated or depressed in pathological conditions. Thus, the level of the identified molecular products is termed per se diagnostic, because the level of the product is diagnostic without any further consideration of the level of any other molecular products in the sample, other than perhaps a normalizing molecular product that is used to normalize the level of the molecular products. One example of such per se diagnostic molecular products are tumor markers.

By contrast, in the data cluster analysis according to the invention, the diagnostic significance of the level of any particular marker, e.g., a protein or transcript is a function of the levels of the other elements that are used to calculate the sample vector. Such products are termed hereinafter as contextual diagnostic products. Thus, in prior implementations of data-mining techniques, the likeness between the biological sample of interest and the learning data set was based on the specified groupings of the biological sample compared to the specified diagnostic molecular products. However, in the invention, the learning algorithm discovers wholly new classification patterns without knowing any prior information about the identity or relationships of the data pattern, i.e., without prior input that a specified diagnostic molecular product is indicative of a particular classification.

The present invention is based, in part, on the unexpectedness or non-obvious discovery of finding hidden contextual diagnostic patterns to yield a classification, e.g., the diagnosis of malignancy in cancers such as carcinomas, melanomas, lymphomas, sarcomas, blastomas, leukemias, myelomas, and neural tumors.

IV. DETAILED DESCRIPTION OF THE INVENTION

The invention comprises a) creating a data stream representing the biological data (or combinations of data streams representing the biological data with clinical, health, or non-biological data) and abstraction of that data into characteristic vectors; b) the discovery of hidden diagnostic patterns of molecular expression (i.e. pattern discovery); and c) determining which biological state of interest such a pattern of molecular expression represents. The molecules of interest may comprise, but are not limited to, proteins, peptides, RNA, DNA, etc. The biological samples comprise, but are not limited to serum, blood, saliva, plasma, nipple aspirants, synovial fluids, cerebrospinal fluids, sweat, urine, fecal matter, tears, bronchial lavage, swabbings, needle aspirantas, semen, vaginal fluids, pre-ejaculate, etc.

The biological states of interest may be a pathologic diagnosis, toxicity state, efficacy of a drug, prognosis of a disease, stage of a disease, biological state of an organ, presence of a pathogen (e.g., a virus), toxicity of one or more drugs, etc. The invention may be used for the diagnosis of any disease in which changes in the patterns of expression of certain molecules like proteins allow it to be distinguished from a non-diseased state. Thus, any disease that has a genetic component in which the genetic abnormality is expressed, one in which the expression of drug toxicity is observed, or one in which the levels of molecules in the body are affected may be studied by the current invention. Such diseases include, but are not limited to, cancers (carcinomas, melanomas, lymphomas (both Hodgkin's and non-Hodgkin's type), sarcomas, blastomas, leukemias, myelomas, and neural tumors, such as glioblastoma, etc.), Alzheimer's disease, arthritis, glomeruulonephritis, autoimmune diseases, etc. Examples of carcinomas include, but are not limited to, carcinomas of the pancreas, kidney, liver and lung; gastrointestinal carcinomas.

The present invention is particularly valuable for the diagnosis of specific diseases for which early diagnosis is important, but is technically difficult because of the absence of symptoms, and for which the disease may be expected to produce differences that are detectable in the serum because of the metabolic activity of the pathological tissue. Thus, the early diagnosis of malignancies are a primary focus of the use of the invention.

The particular components of the invention are described below.

A. Creation of the Data Stream

The data stream can be any reproducible physical or chemical analysis of the biological sample that results in a high throughput data stream. Preferably, the high throughput data stream is characterized by 1,000 or more measurements that can be quantified to at least 1 part per thousand (three significant figures) and more preferably one part in 10,000. There exist numerous methods for the generation of data streams. In one embodiment of the invention when the molecules of interest are proteins or peptides, "time of flight" mass spectra of proteins may be used to generate a data stream. More specifically, matrix assisted laser desorption ionization time of flight (MALDI-TOF) and surface enhanced laser desorption ionization time of flight (SELDI-TOF) spectroscopy may be used when the molecules of interest are proteins or peptides. See generally WO 00/49410. In one embodiment, SELDI-TOF may be used to generate data streams for biological states representing toxicity, and detection of pathogens. In yet another embodiment, data streams may be generated using serially amplified gene expression (SAGE) for gene expression classification. In some circumstances, data streams may be generated using 2-D Gels such as two-dimensional polyacrylamide gel electrophoreses (2D-PAGE).

For clinical pathology, the preferred patient sample for analysis is serum. However, biopsy specimens that are relatively homogenous may also be used. For certain disease states, other fluids can be used, e.g., synovial fluid may be used in the differential diagnosis of arthritis or urine in the differential diagnosis of glomerulonephritis.

The particular proteins that are included in either SELDI-TOF and MALDI-TOF analysis depend upon the surface or matrix that is employed. Lipophylic surfaces such as C-18 alkane surfaces are particularly convenient compared to anionic or cationic surfaces. However, those skilled in the art will appreciate that multiple spectra can be generated from the same sample using different surfaces. These spectra can be concatenated to yield "superspectra" which can be analyzed according to the invention. Likewise, data from two or more high throughput assay methods can also be joined which can be analyzed by the invention. Furthermore, biological data as described in this invention can be joined with clinical, health, or non-biological data.

Whatever surface, matrix or combination of surfaces and matrixes are to be used, great care must be exercised to ensure that the surfaces are uniform from one biological sample to the next.

The data stream can also include measurements that are not inherently organized by a single ordered parameter such as molecular weight, but have an arbitrary order. Thus, DNA microarray data that simultaneously measures the expression levels of 2,000 or more genes can be used as a data stream when the tissue sample is a biopsy specimen, recognizing that the order of the individual genes in the data stream is arbitrary.

Those skilled in the art will appreciate that in keeping with the available commercial embodiments of the instruments, the description of the invention considers the generation of the data stream from a biological sample and the abstraction of the data stream based on the optimal logical chromosome to be two separate processes. However, it is apparent that only routine design choices would allow for the measuring instrument itself to perform the abstracting function. This in no way changes the contribution of the invention to such a diagnostic method and the claims are to be construed as allowing the abstraction and vector analysis portions of the claimed diagnostic method to be performed on different computing devices.

It should be noted that a single data stream from a patient sample can be analyzed for multiple diagnoses using the method of the invention. The additional cost of such multiple analysis would be trivial because the steps specific to each diagnosis are computational only.

B. The Abstraction Process

The first step in the diagnostic process of the invention is the transformation or abstraction of the data stream into a characteristic vector. The data may be conveniently normalized prior to abstraction by assigning the overall peak an arbitrary value of 1.0 and, thus, all other points fractional values. For example, in the embodiment in which the data stream is generated by TOF Mass spectra, the most simple abstraction of TOF mass spectrum consists of the selection of a small number of data points. Those skilled in the art will recognize that more complex functions of multiple points could be constructed, such as averages over intervals or more complex sums or differences between data points that are at predetermined distance from a selected prototype data point. Such functions of the intensity values of the data stream could also be used and are expected to function equivalently to the simple abstract illustrated in the working examples.

Those skilled in the art will also appreciate that routine experimentation can determine whether abstraction by taking the instantaneous slope at arbitrary points could also function in the present invention. Accordingly, such routinely available variations of the illustrated working examples are within the scope of the invention.

C. Pattern Discovery

Pattern discovery is achieved by numerous methods as discussed in the Summary above. However, in a preferred embodiment, the pattern discovery comprises a diagnostic algorithm and a learning algorithm. Thus, in order to practice this embodiment of the invention the routine practitioner must develop a diagnostic algorithm by employing a learning algorithm. To employ the learning algorithm, the routine practitioner uses a training data set and must select two parameters, the number of dimensions and the data cluster size. See U.S. Patent Application titled "Heuristic Method of Classification," (filing date: Jun. 19, 2001, claiming priority of application Ser. No. 60/212,404, filed Jun. 19, 2000).

In one embodiment, the learning algorithm can be implemented by combining two different types of publicly available generic software, which have been developed by others and are well known in the field—a genetic algorithm (J. H. Holland, *Adaptation in Natural and Artificial Systems*, MIT Press 1992) that processes a set of logical chromosomes[1] to identify an optimal logical chromosome that controls the abstraction of the data steam and a adaptive self-organizing pattern recognition system (see, T. Kohonen, *Self Organizing and Associative Memory*, 8 *Series in Information Sciences*, Springer Verlag, 1984; Kohonen, T, *Self-organizing Maps*, Springer Verlag, Heidelberg 1997), available from Group One Software, Greenbelt, Md., which identifies a set of data clusters based on any set of vectors generated by a logical chromosome. Specifically, the adaptive pattern recognition software maximizes the number of vectors that rest in homogeneous data clusters, i.e., clusters that contain vectors of the learning set having only one classification type.

[1] The term logical chromosome is used in connection with genetic learning algorithms because the logical operations of the algorithm are analogous to reproduction, selection, recombination and mutation. There is, of course, no biological embodiment of a logical chromosome in DNA or otherwise. The genetic learning algorithms of the invention are purely computational devices, and should not be confused with schemes for biologically-based information processing.

The genetic algorithm essentially determines the data points which are used to calculate the characteristic vector. However, in keeping with the nomenclature of the art, the list of the specific points to be selected is termed a logical chromosome. The logical chromosome contains as many "genes" as there are dimensions of the characteristic vector. Any set of the appropriate number of data points can be a logical chromosome, provided only that no gene of a logical chromosome is duplicated. The order of the genes has no significance to the invention.

Genetic algorithms can be used when two conditions are met. A particular solution to a problem must be able to be expressed by a set or string of fixed size of discrete elements, which elements can be numbers or characters, and the strings can be recombined to yield further solutions. One must also be able to calculate a numerical value of the relative merit of each solution, namely its fitness. Under these circumstances, the details of the genetic algorithm are unrelated to the problem whose solution is sought. Accordingly, for the present invention any generic genetic algorithm software may be employed. The algorithms PGAPack libraries, available from Argonne National Laboratory is suitable. The calculation of the fitness of any particular logical chromosome is discussed below.

In the illustrative examples, a training data set of about 100 sample data streams was used, each sample data stream containing about 15,000 data points. The genetic algorithms were initialized with about 1,500 randomly chosen logical chromosomes. As the algorithm progressed, the more fit logical chromosomes are duplicated and the less fit are terminated. There is recombination between logical chromosomes and mutation, which occurs by the random replacement of an element of a logical chromosome. It is not an essential feature of the invention that the initially selected collection of logical chromosome be random. Certain pre-screening of the total set of data streams to identify those data points having the highest variability may be useful, although such techniques may also introduce an unwanted initialization bias. The best fitted pattern that survives this process is used to discriminate between biological states and determine the desired classification.

D. The Pattern Recognition Process and Fitness Score Generation

The fitness score of each of the logical chromosomes that are generated by the genetic algorithm is calculated. The calculation of the fitness score requires an optimal set of data clusters be generated for the given logical chromosome. Data clusters are simply the volumes in the vector space in which the characteristic vectors of the training data set rest. The method of generating the optimal set of data clusters is not critical to the invention and will be considered below. However, whatever method is used to generate the data cluster map, the map is constrained by the following rules: (i) each data cluster should be located at the centroid of the data points that lie within the data cluster; (ii) no two data clusters may overlap; and (iii) the dimension of each cluster in the normalized vector space is fixed prior to the generation of the map.

As stated above, to employ the learning algorithm, the routine practitioner must use a learning data set and select two parameters, the number of dimensions and the data cluster size. Both parameters can be set using routine experimentation. Although there is no absolute or inherent upper limit on the number of dimensions in the vector, the learning algorithm itself inherently limits the number of dimensions in each implementation. If the number of dimensions is too low or the size of the cluster is too large, the learning algorithm fails to generate any logical chromosomes that correctly classify all samples into homogeneous clusters, and conversely if the number of dimensions can be too large. Under this circumstance, the learning algorithm generates many logical chromosomes that have the maximum possible fitness early in the learning process and, accordingly, there is only abortive selection. Similarly, when the size of the data clusters is too small, the number of clusters will be found to approach the number of samples in the training data set and, again, the routine practitioner will find that a large number of logical chromosomes will yield the maximum fitness.

Those skilled in the art understand that a training data set can nearly always be assigned into homogeneous data clusters. Thus, the value of the diagnostic algorithm generated by a learning algorithm must be tested by its ability to sort a set of data other than the training data set. When a learning algorithm generates a diagnostic algorithm that successfully assigns the training data set but only poorly assigns the test data set, the training data is said to be overfitted by the learning algorithm. Overfitting results when the number of dimensions is too large and/or the size of the data clusters is too small.

The method used to define the size of the data cluster is a part of the invention. The cluster size is defined by the maximum of the equivalent the Euclidean distance (root sum of the squares) between any two members of the data cluster. A data cluster size that corresponds to a requirement of 90% similarity is suitable for the invention when the data stream is generated by SELDI-TOF mass spectroscopy data. Mathematically, 90% similarity is defined by requiring that the distance between any two members of a cluster is less than 0.1 of the maximum distance between two points in a normalized vector space. For this calculation, the vector space is normalized so that the range of each scalar of the vectors within the training data set is between 0.0 and 1.0. Thus normalized, the maximal possible distance between any two vectors in the vector space is then root N, where N is the number of dimensions. The Euclidean diameter of each cluster is then 0.1×root (N).

The specific normalization of the vector space is not a critical feature of the method. The foregoing method was selected for ease of calculation. Alternative normalization can be accomplished by scaling each dimension not to the range but so that each dimension has an equal variance.

Those skilled in the art will further recognize that the data stream may be converted into logarithmic form if the distribution of values within the data stream is log normal and not normally distributed.

Once the optimal set of data clusters for a logical chromosome has been generated, the fitness score for that chromosome can be calculated. For the present invention, the fitness score of the chromosome roughly corresponds to the number of vectors of the training data set that rest in clusters that are homogeneous, i.e., clusters that contain the characteristic vectors from samples having a single diagnosis. More precisely, the fitness score is calculated by assigning to each cluster a homogeneity score, which varies, for example, from 0.0 for homogeneous clusters to 0.5 for clusters that contain equal numbers of malignant and benign sample vectors. The fitness score of the chromosome is the average fitness score of the data clusters. Thus, a fitness score of 0.0 is the most fit. There is a bias towards logical chromosomes that generate more data clusters, in that when two logical chromosomes that have equal numbers of errors in assigning the data, the chromosome that generates the more clusters will have a lower average homogeneity score and thus a better fitness score.

A preferred technique for generating for generating data clusters is using the self-organizing map algorithm as developed by Kohonen. (Kohonen, T, Self-organizing maps, Springer Verlag, Heidelberg 1997). This type of technique is variously termed a "Lead Cluster Map" ("LCM") or an "Adaptive Feature Map" can be implemented by generic software that is publicly available. Suitable vendors and products include Model 1 from Group One Software (Greenbelt, Md.) and Adaptive Fuzzy Feature Map (American Heuristics Corp.). The LCM has significant advantages in that it is a) it is a non-linear modeling method; b) the number of independent variables is virtually unlimited; and c) compared to other non-linear modeling techniques, the LCM has the advantage of being adaptive. It can detect novel patterns in the data stream and track rare patterns. This is particularly important in classification of biological states, viz, mutations to viruses.

E. Description and Verification of Specific Embodiments
1. Development of a Diagnostic for Prostatic Cancer Using the above-described learning algorithm, the current invention was employed to develop a diagnostic for prostatic cancer using SELDI-TOF mass spectra (MS) of 55 patient serum samples, 30 having biopsy diagnosed prostatic cancer and prostatic serum antigen (PSA) levels greater than 4.0 ng/ml and 25 normals having PSA levels below 1 ng/ml. The MS data was abstracted by selection of 7 molecular weight values (2092, 2367, 2582, 3080, 4819, 5439 and 18,220 Da). The specific molecular weights are not a critical parameter of the invention and may varying depending on the absorptive surface. A cluster map that assigned each vector in the training data set to a homogeneous data cluster was generated. The cluster map contained 34 clusters, 17 benign and 17 malignant.

The diagnostic algorithm was tested using 231 samples that were excluded from the training data set. Six sets of samples from patients with various clinical and pathological diagnoses were used. The clinical and pathological description and the algorithm results were as follows: 1) 24 patients with PSA>4 ng/ml and biopsy proven cancer, 22 map to diseased data clusters, 2 map to no cluster; 2) 6 normal, all map to healthy clusters; 3) 39 with benign hypertrophy (BPH) or prostatitis and PSA<4 ng/ml, 7 map to diseased data clusters, none to healthy data clusters and 32 to no data cluster; 4) 139 with BPH or prostatitis and PSA>4 and <10 ng/ml, 42 map to diseased data clusters, 2 to healthy data clusters and 95 to no data cluster; 5) 19 with BPH or prostatitis and PSA>10 ng/ml, 9 map to diseased data clusters none to healthy and 10 to no data cluster. A sixth set of data was developed by taking pre- and post-prostatectomy samples from patients having biopsy proven carcinoma and PSA>10 ng/ml. As expected, each of the 7 pre-surgical samples was assigned to a diseased data set. However, none of the sample taken 6 weeks post surgery, at a time when the PSA levels had fallen to below 1 ng/ml, were not assignable to any data set. These results are summarized in Table 1.

When evaluating the results of the foregoing test, it should be recalled that the rate of occult carcinoma in patients having PSA of 4–10 ng/ml and benign biopsy diagnosis is about 30%. Thus, the finding that between 18% and 47% of the patients with elevated PSA, but no tissue diagnosis of cancer, is consistent with a highly accurate assay that correctly predicts the presence of carcinoma.

Of greater present interest is the fact that the diagnostic algorithm is able to classify a significant fraction of the samples in 3), 4) and 5) to a non-cancerous, non-normal category despite the fact that such category was not presented during training. Indeed, the fact that any samples from this group would necessarily include a substantial number with occult carcinoma carriers argues that BPH or prostatitis samples should not be included in the training data set.

TABLE 1

| STUDY SET | N | PREDICTED PHENOTYPE | | |
|---|---|---|---|---|
| | | CANCER (%) | NORMAL (%) | OTHER (%) |
| Biopsy proven cancer (PSA > 4 ng/ml)[a] | 24 | 22 (92%) | 0 (0%) | 2 (8%) |
| Control Men (PSA < 1 ng/ml) | 6 | 0 (0%) | 6 (100%) | 0 (0%) |
| Biopsy proven BPH/Prostatitis (PSA < 4 ng/ml) | 39 | 7 (18%) | 0 (0%) | 32 (82%) |
| Biopsy proven BPH/Prostatitis[b] (PSA 4–10 ng/ml) | 139 | 42 (30%) | 2 (1%) | 95 (68%) |

TABLE 1-continued

|  |  | PREDICTED PHENOTYPE | | |
| --- | --- | --- | --- | --- |
| STUDY SET | N | CANCER (%) | NORMAL (%) | OTHER (%) |
| Biopsy proven BPH/Prostatitis (PSA > 10 ng/ml) | 19 | 9 (47%) | 0 (0%) | 10 (52%) |
| Biopsy proven cancer PRE-SURGERY[c] (PSA > 10 ng/ml) | 7 | 7 (100%) | 0 (0%) | 0 (0%) |
| Biopsy proven cancer POST-SURGERY[c,d] (PSA < 1 ng/ml) | 7 | 0 (0%) | 0 (0%) | 7 (100%) |

[a]Male subjects entered in screening trial; entrance criteria: >50 years old, asymptomatic. Biopsy conducted if PSA > 4 ng/ml or a positive digital rectal exam. Includes 6 patients with PSA > 10 ng/ml and 18 patients with PSA 4–10 ng/ml.
[b]30–35% occult cancer expected
[c]Patient-matched
[d]Serum taken at six-week post-surgery follow-up 2. Development of a Diagnostic for Ovarian Cancer The above described methods were employed to generate a diagnostic algorithm for ovarian carcinoma again using SELDI-TOF MS analysis of patient serum. A training set of 100 samples was used to construct a cluster set map. The MS data was abstracted by selection of 5 molecular weights (531, 681, 903, 1108 and 2863 m/e). A cluster map consisting of 15 disease clusters and 11 healthy clusters was constructed. Of the 50 samples in the training data set having proven ovarian cancer, 40 were assigned to diseased data clusters, leaving 10 false negative; of the 50 samples from normals, 44 were assigned to healthy data clusters leaving 6 false positives.

It was observed that for each of the selected molecular weights, the range of values of the healthy and diseased data clusters overlapped. Indeed, for 4 of the 5 molecular weights, the range for the diseased encompassed the range for the healthy data clusters. Additionally, the diagnostic patterns being detected were not caused by tumor markers, but rather by contextual diagnostic products.

The diagnostic algorithm was tested using a further 100 samples, which were divided into three clinical, pathological groups. The groups and the algorithm results were as follows: 1) 50 samples from patients with no disease, 47 were assigned to healthy data clusters and 3 to disease data clusters; 2) 32 patients with ovarian carcinoma Stages II, III or IV, all of which were assigned to diseased data clusters; and 3) 18 patients with ovarian carcinoma stage I, all of which mapped to diseased data clusters. These results are summarized in Table 2.

TABLE 2

| Cohort | N | Predicted Cancer | Predicted Negative | Accuracy |
| --- | --- | --- | --- | --- |
| No Evidence of Disease | 50 | 3 | 47 | 94% |
| Biopsy Proven Ovarian Cancer Stage II, III, IV | 32 | 32 | 0 | 100% |
| Biopsy Proven Ovarian Cancer Stage I | 18 | 18 | 0 | 100% |

3. Sensitivity for Early Stage Disease

A set of randomly chosen sera (50 from the control cohort and 50 sera from the disease cohort) within the ovarian cancer study set of 200 specimens was selected for SELDI-TOF mass spectrometry analysis and subsequent training of the bioinformatics method. A pattern of mass intensities at 5 independent molecular weight regions of 534, 989, 2111, 2251, and 2465 Da discovered from a starting set of $15,000^5$ pattern permutations correctly segregated 98% (49/50) of the ovarian cancer samples and 94% of the controls (47/50) in the training set. The optimal proteomic pattern, challenged with 100 SELDI-TOF data streams from diagnosis-blinded cases was able to accurately predict the presence of ovarian cancer in all 50 cancer specimens contained within the 100 unknown test samples (50/50, 95% confidence interval 93% to 100%). This included the correct classification of 18/18 stage I cancers (95% confidence interval 82% to 100%) while maintaining specificity for the blinded cancer-free samples (47/50, 95% confidence interval 84% to 99%, overall $p<10^{-10}$ by chi-squared test). These results support the hypothesis that low molecular weight proteomic patterns in sera reflect changes in the pathology of tissue within an organ at a distant site. Moreover, such patterns may be sensitive indicators of early pathological changes, since they correctly classified all 18 sera from organ-confined stage I ovarian cancer specimens.

4. Specificity, Prediction and Discrimination of the Presence of Prostate Cancer and Benign Prostate Hypertrophy Initially, the current invention was challenged to find a pattern of proteins that could discriminate the sera from men with biopsy-proven prostate cancer from sera derived from asymptomatic aged-matched males. The training set was comprised of 56 sera, 31 from asymptomatic men with biopsy-proven prostate cancer (PSA>4 ng/ml, avg. 14.5 ng/ml), and 25 age-matched men with no evidence of prostate cancer (PSA<1 ng/ml, avg. 0.3 ng/ml). The 56 sera were analyzed by SELDI-TOF. The pattern discovery analysis found a signature pattern of the combined normalized intensities of 7 protein peaks (out of $15,000^7$ possible permutations) at the specific molecular weights of 2092, 2367, 2582, 3080, 4819, 5439, and 18220 Da that could distinguish all 56 samples analyzed in the prostate sera training set.

After training, the optimal proteomic pattern was tested with 227 blinded sera samples. The blinded study set contained a) 24 sera from asymptomatic men who had subsequent biopsy-proven cancer, and whose PSA values were between 4–10 ng/ml at the time of collection, b) control sera from 6 age-matched males (PSA<1 ng/ml) and c) 197 sera from men with biopsy-proven benign prostatic hypertrophy or prostatitis (PSA values ranged from 0.4 ng/ml to 36 ng/ml).

Using the prostate signature pattern, the data-mining tool was able to accurately predict the presence of prostate cancer in the blinded test set (92%, 22/24, p<0.000001 compared to patients with BPH), including 17/18 containing PSA values of 4–10 ng/ml. Importantly 70% of the patients (137/197) with biopsy proven BPH were classified as belonging to a unique (non-normal, non-cancer) phenotype. Only 1% of the sera from the BPH-positive cohort was categorized as a normal phenotype. When sera from 6 healthy controls were compared to those of the 24 patients with biopsy proven cancer, 6/6 healthy patients were classified correctly, compared to 22/24 patients with prostate cancer (p<0.000001). In addition, a statistically significant trend emerged in the relationship between increasing PSA levels (normal, BPH with increasing PSA) and increasing classification of severity of disease ($p=1.4\times10^{-4}$). The optimized prostate signatures reverted from a cancerous to a non-cancerous (but not normal) phenotype in a blinded set of matched sera from patients who underwent curative prostate resection in 7 of 7 subjects (p=0.016; 95% confidence interval 59% to 100%).

5. Sample Source Preparation and Analysis a. Ovarian Cancer

The anonymized ovarian screening serum study set was obtained from the Early Detection Research Network ("EDRN") National Ovarian Cancer Early Detection Program according to full Institutional Review Board ("IRB") oversight. This set contained sera from 200 asymptomatic women, 100 with ovarian cancer at the time of sample collection and 100 control women at risk for ovarian cancer as defined by family history or previous breast cancer diagnosis (Table 3). This group of unaffected women had been followed and was disease-free for at least five years. All sera were obtained prior to diagnosis and intervention. The disease cohort included histology confirmed papillary serous, endometrioid, clear cell, mucinous, adenocarcinoma, and mixed ovarian cancers of all stages. All women in the disease cohort underwent extensive surgical exploration and formal FIGO staging.

TABLE 3

| PANEL SET | Total Patients | Training Subset | Unknown Test Set | DIAGNOSIS |
|---|---|---|---|---|
| Ovarian Cancer Screening Clinic | 100 | 50 | 50 | No Evidence of disease: 5 year follow-up. |
|  | 100 | 50 | 50 | Path Dx: Ovarian Cancer |
| Prostate Cancer Screening Clinic | 31 | 25 | 6 | No evidence of disease: PSA < 1.0 ng/mL |
|  | 55 | 31 | 24 | Path Dx: Prostate Cancer: PSA > 4.0 ng/mL |
|  | 197 | 0 | 197 | Path Diagnosis: BPH/Prostatitis |
|  | 7 | 0 | 7 | Biopsy proven cancer PRE-SURGERY |
|  | 7 | 0 | 7 | Biopsy proven cancer Post-SURGERY | b. Prostatic Cancer

The anonymized prostate screening serum study set was obtained from a prostate cancer-screening clinic where samples were obtained under approved informed consent (277 samples) (Table 3). An additional 20 anonymized specimens were collected at the National Cancer Institute under IRB approved informed consent. The Chilean trial was initiated in 1996 and lasted for 5 years. The subject eligibility criteria required asymptomatic men over the age of 50 with no previous history of prostate cancer. All men provided a serum sample and then received a medical evaluation and a digital rectal examination. Subsequently, men with a serum PSA>4.0 ng/ml, or suspicious digital rectal examinations were subjected to a single core needle biopsy for pathologic diagnosis. The prostate adenocarcinomas represented were of a full spectrum of grades (I–III) and Gleason scores (4–9). The 20 sera acquired at the NCI were taken from a) 7 men at the time of diagnosis and six weeks after prostatectomies for biopsy-proven organ confined prostate cancer and b) 6 normal healthy male volunteers, PSA<1.0 ng/ml. All sera were obtained prior to medical examination, diagnosis, and treatment. All sera were collected, spun down, aliquoted and stored in liquid nitrogen until use. Received sera were thawed once, separated into 10 microliter aliquots, and then refrozen in liquid nitrogen until SELDI-TOF analysis was performed.

5. Proteomic Analysis

Sera were thawed and used once to generate protein mass signatures on the Protein Biology System 1 SELDI-TOF mass spectrometer (Ciphergen Biosystems, Freemont, Calif.). External mass calibration was accomplished using angiotensin I (amino acid sequence 1-10) and bovine cytochrome c (Ciphergen Biosystems, Freemont, Calif.) with respective masses of 1296.5 Da and 12230.9 Da. Protein profiles of all proteins that can bind to the C18 reverse-phase hydrophobic interaction surface within the 1000–20,000 Da mass range were generated. The organic acid matrix surface was α-cyano-4-hydroxy-cirnamic acid (CHCA). This matrix is required to co-crystallize with the protein mixture for full protein ionization off of the selected bait.

Sample preparation: One microliter of acetonitrile (Sigma-Aldrich Co., St. Louis, Mo.) was added to the sample spots of the 8-feature C18 hydrophobic interaction protein chip (Ciphergen Biosystems, Inc., Freemont, Calif.). This chip will bind proteins through hydrophobic interactions that are dependent upon the intrinsic primary amino acid sequences specific for every protein. The acetonitrile application was followed by the addition of 1 $\mu$l of serum. The sample was allowed to air dry on the chip. The chips were vigorously washed by vortexing in deionized water for 4 minutes and allowed to air dry. Lastly, 0.5 $\mu$l of CHCA solution was added. After the matrix solution dried, an additional 0.5 $\mu$l of matrix was applied to each sample and allowed to air dry. The C18 chip was chosen because it was found to consistently and reproducibly produce the greatest number of different protein and peptide signatures (data not shown). SELDI-TOF, like other time-of-flight spectrometric techniques, has its best sensitivity at the low molecular weight range (<20,000 Da). Data were recorded and optimized for analysis with the SELDI Protein Biology System version 2.0 software (Ciphergen Biosystems, Inc., Palo Alto, Calif.). Raw SELDI data, not filtered or scaled in any way, were converted to ASCII data files for analysis by the data-mining tool.

6. Detection of Drug Toxicity

The method of the invention was tested on data streams obtained from biological samples from rats treated with doxorubicin that developed proven cardiotoxicity. Controls were treated with saline. The biological samples obtained from rats showing cardiotoxicity were classified correctly with 100% selectivity and 100% sensitivity and no false positives. See Table 4.

TABLE 4

| Count – Actual | Actual | | |
|---|---|---|---|
| Score | 0 | 1 | Total Result |
| 0 | 29 |  | 29 |
| 1 | 1 | 7 | 8 |
| Total Result | 30 | 7 | 37 |
|  | Sensitivity | 100.00% |  |
|  | Selectivity | 0.00% |  |

7. Detection of Drug Treatment

Rats were treated with doxorubicin and a cardioprotectant. Thus, some animals had toxicity while others did not. Table 8 shows that using the method of the invention all but one of the treated animals could be correctly identified, while only misclassifying 2 control animals. See Table 5.

TABLE 5

| Count – Actual | Actual | | |
|---|---|---|---|
| Score | 0 | 1 | Total Result |
| 0 | 15 |  | 15 |
| 0.1 | 10 | 1 | 11 |
| 0.56 | 2 | 4 | 6 |
| 1 |  | 13 | 13 |
| Total Result @ Score =0.56 | 27 | 18 | 45 |
|  | Sensitivity | 94.44% |  |
|  | Selectivity | 10.53% |  |

8. Detection of Virus

Simian Foamy Virus was detected in cell lysates. Lysates from infected cells were correctly classified 80% of the time (8/10) with no false positives. See Table 6.

TABLE 6

| Count – Actual | Actual | | |
| --- | --- | --- | --- |
| Score | 0 | 1 | Total Result |
| 0 | 9 | | 9 |
| 0.5 | 3 | 2 | 5 |
| 0.8 | | 6 | 6 |
| 1 | | 2 | 2 |
| Total Result @ Score =0.8 | 12 Sensitivity Selectivity | 10 80.00% 0.00% | 22 |

9. Use of a Windowing Technique for Ovarian Cancer

Initial reduction to practice was based on a simple trial and error selection of groups of 100 contiguous features in the proteomic data stream. An adaptive pattern recognition algorithm, the Lead Cluster Map, (LCM) was employed. Sampling of the data stream started at a different point in the data stream for each run. A run consisted of collection of 14–15 collections of 100 features. After a series of 25 runs, the best models accurately predicted the correct biological state 80% with a false positive rate of approximately 30%. These results demonstrate the effectiveness of using proteomic patterns in the classification of biological states. Indeed, models with this level of accuracy would be well suited for batch screening of potentially therapeutic compounds. See Table 7.

TABLE 7

| Count – Actual | Actual | | |
| --- | --- | --- | --- |
| Score | 0 | 1 | Total Result |
| 0 | 18 | 3 | 21 |
| 0.25 | 10 | 1 | 11 |
| 0.29 | 5 | 6 | 11 |
| 0.33 | 5 | 5 | 10 |
| 0.5 | 6 | 6 | 12 |
| 0.67 | 2 | 11 | 13 |
| 1 | 4 | 18 | 22 |
| Total Result | 50 Sensitivity @ 0.33 Specificity @ 0.33 | 50 80% 29.82% | 100 |

10. Detection of Breast Cancer

Nipple aspirants taken from breast cancer patients were analyzed using the process of the invention. The nipple aspirants were subjected to a mass spectral analysis and subjected to a pattern finding method. A sensitivity of nearly 92% was observed. See Table 8.

TABLE 8

| Count – Actual | Actual | | |
| --- | --- | --- | --- |
| Score | 0 | 1 | Total Result |
| 0 | 7 | 2 | 9 |
| 0.5 | 3 | | 3 |
| 0.67 | | 5 | 5 |
| 1 | | 6 | 6 |
| Total Result | 10 | 13 | 23 |

TABLE 8-continued

| Count – Actual | Actual | | |
| --- | --- | --- | --- |
| Score | 0 | 1 | Total Result |
| Sensitivity @ 0.67 Selectivity @ 0.67 | | 91.67% 0.00% | |

What is claimed is:

1. A method of determining whether a biological sample taken from a subject indicates that the subject has a disease by analyzing a data stream that is obtained by performing an analysis of the biological sample, comprising:

abstracting the data stream to produce a sample vector that characterizes the data stream in a predetermined vector space containing a diagnostic cluster, the diagnostic cluster being a disease cluster, the disease cluster corresponding to the presence of the disease;

determining whether the sample vector rests within the disease cluster; and if the sample vector rests within the diseased cluster, identifying the biological sample as indicating that the subject has the disease, and displaying the result.

2. The method of claim 1, wherein the data stream is data describing an expression of molecules in the biological sample.

3. The method of claim 2, wherein the molecules are proteins.

4. The method of claim 2, wherein the molecules are selected from the group consisting of proteins, peptides, phospholipids, DNA, and RNA.

5. The method of claim 2, wherein the biological sample is serum.

6. The method of claim 2, wherein the biological sample is selected from the group consisting of serum, blood, saliva, plasma, nipple aspirants, synovial fluids, cerebrospinal fluids, sweat, urine, fecal matter, tears, bronchial lavage, swabbings, needle aspirants, semen, vaginal fluids, and pre-ejaculate.

7. The method of claim 2, wherein the biological sample is selected from the group consisting of tissue culture supernatants, lyophilized tissue cultures, and viral cultures.

8. The method of claim 1, wherein the disease is one in which the patterns of expression of inherent molecules in the diseased state are different from those in the non-diseased state.

9. The method of claim 1, wherein the disease is a cancer.

10. The method of claim 9, wherein the cancer is breast cancer.

11. The method of claim 9, wherein the cancer is a carcinoma.

12. The method of claim 9, wherein the cancer is selected from the group consisting of carcinomas, melanomas, lymphomas, sarcomas, blastomas, leukemias, myelomas, and neural tumors.

13. The method of claim 9, wherein the cancer is a carcinoma, said carcinoma being a prostatic carcinoma.

14. The method of claim 9, wherein the cancer is a carcinoma, said carcinoma being an ovarian carcinoma.

15. The method of claim 1, wherein the disease is selected from the group consisting of auto-immune diseases, Alzheimer's disease and arthritis.

16. The method of claim 1, wherein the disease is glomerulonephritis.

17. The method of claim 1, wherein the disease is any infectious disease.

18. The method of claim 1, wherein the data stream is formed by any high throughput data generation method.

19. The method of claim 1, wherein the data stream is based on data associated with a time of flight mass spectrum.

20. The method of claim 19, wherein the time of flight mass spectrum is generated by surface-enhanced laser desorption time-of-flight mass spectroscopy.

21. The method of claim 19, wherein the time of flight mass spectrum is generated by matrix assisted laser desorption ionization time of flight.

22. The method of claim 1, wherein the data stream is based on data associated with a spectrum.

23. The method of claim 1, wherein the data stream is based on data associated with a mass spectrum.

24. The method of claim 1, wherein the diagnostic cluster is a first diagnostic cluster, the vector space contains a second diagnostic cluster, the second diagnostic cluster is a healthy cluster, the healthy cluster corresponding to an absence of the disease, further comprising:

determining whether the sample vector rests within the healthy cluster; and if the sample vector rests within the healthy cluster, identifying the biological sample as indicating that the subject does not have the disease, and displaying the result.

25. A method of determining whether a biological sample taken from a subject indicates that the subject does not have a disease by analyzing a data stream that is obtained by performing an analysis of the biological sample, comprising:

abstracting the data stream to produce a sample vector that characterizes the data stream in a predetermined vector space containing a diagnostic cluster, the diagnostic cluster being a healthy cluster, the healthy cluster corresponding to the absence of the disease;

determining whether the sample vector rests within the healthy cluster; and if the sample vector rests within the healthy cluster, identifying the biological sample as indicating that the subject does not have the disease, and displaying the result.

26. The method of claim 25, wherein the data stream is data describing an expression of molecules in the biological sample.

27. The method of claim 26, wherein the molecules are proteins.

28. The method of claim 26, wherein the molecules are selected from the group consisting of proteins, peptides, phospholipids, DNA, and RNA.

29. The method of claim 26, wherein the biological sample is serum.

30. The method of claim 26, wherein the biological sample is selected from the group consisting of serum, blood, saliva, plasma, nipple aspirants, synovial fluids, cerebrospinal fluids, sweat, urine, fecal matter, tears, bronchial lavage, swabbings, needle aspirants, semen, vaginal fluids, and pre-ejaculate.

31. The method of claim 26, wherein the biological sample is selected from the group consisting of tissue culture supernatants, lyophilized tissue cultures, and viral cultures.

32. The method of claim 25, wherein the disease is one in which the patterns of expression of inherent molecules in the diseased state are different from those in the non-diseased state.

33. The method of claim 25, wherein the disease is a cancer.

34. The method o claim 33, wherein the cancer is breast cancer.

35. The method of claim 33, wherein the cancer is a carcinoma.

36. The method of claim 33, wherein the cancer is selected from the group consisting of carcinomas, melanomas, lymphomas, sarcomas, blastomas, leukemias, myelomas, and neural tumors.

37. The method of claim 33, wherein the cancer is a carcinoma, said carcinoma being a prostatic carcinoma.

38. The method of claim 33, wherein the cancer is a carcinoma, said carcinoma being an ovarian carcinoma.

39. The method of claim 25, wherein the disease is selected from the group consisting of auto-immune diseases, Alzheimer's di ease and arthritis.

40. The method of claim 25, wherein the disease is glomerulonephritis.

41. The method of claim 25, wherein the disease is any infectious disease.

42. The method of claim 25, wherein the data stream is formed by any high throughput data generation method.

43. The method of claim 25, wherein the data stream is based on data associated with a time of flight mass spectrum.

44. The method of claim 43, wherein the time of flight mass spectrum is generated by surface-enhanced laser desorption time-of-flight mass spectroscopy.

45. The method of claim 43, wherein the time of flight mass spectrum is generated by matrix assisted laser desorption ionization time of flight.

46. The method of claim 25, wherein the data stream is based on data associated with a spectrum.

47. The method of claim 25, wherein the data stream is based on data associated with a mass spectrum.

48. The method of claim 25, wherein the diagnostic cluster is a first diagnostic cluster, the vector space contains a second diagnostic cluster, the second diagnostic cluster is a disease cluster, the disease cluster corresponding to a presence of the disease, further comprising:

determining whether the sample vector rests within the disease cluster; and if the sample vector rests within the disease cluster, identifying the biological sample as indicating that the subject has the disease, and displaying the result.

* * * * *

UNITED STATES PATENT AND TRADEMARK OFFICE
CERTIFICATE OF CORRECTION

PATENT NO. : 6,925,389 B2
APPLICATION NO. : 09/906661
DATED : August 2, 2005
INVENTOR(S) : Ben A. Hitt et al.

It is certified that error appears in the above-identified patent and that said Letters Patent is hereby corrected as shown below:

Column 20,
Line 10, replace "o" with --of--.
Line 24, replace "di ease" with --disease--.

Signed and Sealed this

Twenty-second Day of August, 2006

JON W. DUDAS
*Director of the United States Patent and Trademark Office*